United States Patent [19]  
Dolfini et al.

[11] Patent Number: 4,871,881  
[45] Date of Patent: Oct. 3, 1989

[54] HYDROLYSIS OF ACTIVATED OLEFINIC KETONES AND ALDEHYDES

[75] Inventors: Joseph E. Dolfini; Jerome Glinka, both of Cincinnati, Ohio

[73] Assignee: Mallinckrodt, Inc., St. Louis, Mo.

[21] Appl. No.: 313,025

[22] Filed: Feb. 21, 1989

Related U.S. Application Data

[60] Division of Ser. No. 123,137, Nov. 20, 1987, which is a continuation-in-part of Ser. No. 10,902, Feb. 4, 1987, Pat. No. 4,709,098.

[51] Int. Cl.$^4$ ............................................. C07C 45/42
[52] U.S. Cl. .................... 568/491; 568/449; 568/485
[58] Field of Search ................... 568/491, 449, 485

[56] References Cited

U.S. PATENT DOCUMENTS

| 1,999,620 | 4/1935 | Van Peski et al. | 568/491 |
| 2,623,905 | 12/1952 | Pines et al. | 568/491 |
| 3,833,659 | 9/1974 | Schmerling et al. | 568/491 |
| 4,617,419 | 10/1986 | Wiener et al. | |
| 4,709,098 | 11/1987 | Dolfini et al. | 568/491 |
| 4,810,824 | 3/1989 | Dolini et al. | 568/491 |

FOREIGN PATENT DOCUMENTS

| 875512 | 7/1949 | Fed. Rep. of Germany | 568/491 |
| 927688 | 5/1955 | Fed. Rep. of Germany | 568/491 |
| 946443 | 8/1956 | Fed. Rep. of Germany | 568/491 |
| 1519093 | 7/1978 | United Kingdom | 568/491 |

Primary Examiner—Werren B. Lone  
Attorney, Agent, or Firm—Wood, Herron & Evans

[57] ABSTRACT

Ketones or aldehydes containing one or more carbon-carbon double bonds and a carbonyl group conjugated with at least one double bond are hydrolyzed by the action of heat and pressure in the presence of water by a batch or continuous process. The ketone or aldehyde cleaves at the double bond conjugated with the carbonyl group to produce additional carbonyl-containing compounds.

6 Claims, No Drawings

HYDROLYSIS OF ACTIVATED OLEFINIC KETONES AND ALDEHYDES

RELATED APPLICATION

This is a division of application Ser. No. 123,137 filed Nov. 20, 1987, which in turn is a continuation-in-part of application Ser. No. 10,902 filed Feb. 4, 1987 and issued Nov. 24, 1987 under U.S. Pat. No. 4,709,098.

BACKGROUND OF THE INVENTION

In the field of organic chemistry, reaction products different in form from their starting materials can be obtained by means of a large number of reaction sequences. Organic starting materials particularly amenable to reaction are alkene compounds, otherwise known as olefins. Olefins are characterized by the presence of one or more carbon-carbon double bonds. Reactions involving olefins usually occur at the carbon-carbon double bonds. The double bond can be eliminated by addition of atoms to the olefin molecule. The double bond can also be shifted from one carbon-carbon couple to another within the molecule. The double bond can also be cleaved to form two or more smaller molecules from one olefin molecule having one or more double bonds. Cleavage is accomplished by a small number of reaction sequences such as ozonolysis, oxidation and the like. Generally, cleavage occurs by the addition of oxygen to the double bond carbons which then destroys the bond between the carbons.

The presence of a substituent group on the olefin compound sometimes permits the double bond to be broken under less vigorous conditions. One such substituent is the carbonyl group, which consists of a carbon doubly bonded to oxygen. A carbonyl group having its double bond conjugated with the olefin double bond can activate the olefin double bond and cause it to break in the presence of alkaline catalyst, heat and water. This reaction is known as a reverse or retro-aldol condensation which are subject to side reactions and reaction product condensations. In the presence of only heat and water, typically no reaction occurs.

One reference has been found which describes the cleavage of a substituted conjugated cyclohexanone molecule in the presence of heat, pressure and water without any added alkaline catalyst. The reaction as cited in *Annalen*, Vol. 289, p. 337 (1896), involved the formation of acetone and 3-methyl-cyclohexanone in an autoclave at 250° C. from pulegone and water. No other references of cleavage using only heat, pressure and water are known; further, it is believed that pulegone underwent reaction under the above conditions because the position of the substituents on the cyclohexyl ring caused a destabilization of the olefin, permitting reaction to occur.

SUMMARY OF THE INVENTION

It has now been found that certain acyclic compounds having at least one carbon-carbon double bond and a conjugated carbonyl carbon-oxygen bond can undergo a cleavage reaction in the absence of alkaline catalyst. Specifically, it has been found that acyclic unsaturated ketones and aldehydes having a carbon-carbon double bond conjugated with the carbonyl double bond undergo hydrolysis in the presence of heat, pressure, and water which breaks the conjugated carbon-carbon double bond and forms new carbonyl-containing reaction products. Also, the hydrolysis reaction causes cleavage of a substantial portion of the starting material in practical yield. The hydrolysis of the alpha, beta-unsaturated compound as practiced by this invention actually proceeds contrary to the normal acid or base catalyzed aldol reaction sequence. The favored sequence would produce an alpha, eta-unsaturated compound from the carbonyl-containing compounds with formation of water. One of the advantages of this invention is the production of natural flavors from natural sources simply under the reaction conditions of temperature, pressure, and water with no catalysts.

In the above application Serial No. 10,902, it had been reported that the reaction proceeds in the presence of water with a temperature in the range of about 200° to about 300° C. and pressure in the range of about 225 to about 1250 psi. It has also been found that the hydrolysis reaction can be effectively conducted at even higher temperatures and pressures at about 325° C. and 2000 psi. It is preferred to conduct the reaction at a temperature of at least about 200° C. and a pressure of at least about 225 psi. Minor variations in temperature or pressure during the reaction have no significant effect on the generation of product and therefore can be tolerated. Thus, in a broader aspect this invention is directed to the method of hydrolysis of the above class of compounds at substantially neutral pH in the presence of water and heating at a superatmospheric pressure sufficient to effect said hydrolysis. As used herein "superatmospheric" means above normal atmospheric pressure conditions, usually on the order of about 225 to about 2000 psi. It is critical that the starting material and water be subjected to both pressure and temperature in the above-listed ranges at a satisfactory superatmospheric temperature and pressure. Starting material and water subjected only to heat or only to pressure will not produce hydrolyzed products. The water may be distilled or deionized, but tap water is also sufficient.

The starting materials intended to be included within this invention are acyclic unsaturated ketones and aldehydes having one or more carbon-carbon double bonds wherein at least one carbon-carbon double bond is conjugated with the carbonyl carbon-oxygen double bond. The term "acyclic" is meant to limit the class of compounds t those wherein neither the carbonyl carbon nor either of the carbons of the conjugated carbon-carbon double bond are also integral components of a ring structure, either cyclic or aromatic. Cyclic or aromatic substituents may exist in the same molecule, however.

The hydrolysis reaction claimed herein is typically carried out in an autoclave in a batch-type process. However, the reaction may be successfully accomplished in a continuous flow reactor, such as a tube reactor.

Because of the nature of the hydrolysis reaction, non-reactive species present in the starting material will have little effect on the cleavage of the conjugated carbon-carbon double bond. As a result, natural sources of the acyclic unsaturated ketones and aldehydes may be employed to obtain products in substantial yield.

DETAILED DESCRIPTION

The method in its broader aspects is practiced by hydrolyzing activated acyclic olefins as represented by the following chemical equation:

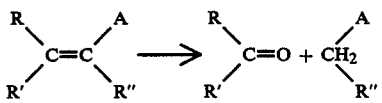

The substituents R, R' and R" are hydrogen, alkyl, cycloalkyl or aryl hydrocarbon radical or substituted alkyl, cycloalkyl or aryl hydrocarbon radical. The substituent A is a radical selected from the class of aldehyde or ketone which is conjugated with the olefin; R" can also be an A. The reaction proceeds in the presence of water at a substantially neutral pH at superatmospheric pressure and temperature, for example, under pressure in the range of about 225 to about 2000 psi and at a temperature in the range of about 200° to about 325° C., preferably at least about 225 psi and about 200° C.

A large number of activated olefin compounds may be hydrolyzed according to the teachings of this invention. The compounds in the following non-comprehensive list are included under the description of hydrolyzable activated olefin compounds: cinnamaldehyde to produce benzaldehyde; citral to produce 6-methyl-5-hepten-2-one; 2,4-decadienal to produce hexanal; 3-decen-2-one to produce heptanal and acetone; 2-dodecenal to produce decanal; 1,2-dibenzoylethylene to produce acetophenone; 1,7-bis (4-hydroxy-3-methoxyphenyl)-1,6-heptadiene-3,5-dione to produce 4-hydroxy-3-methoxybenzaldehyde; 2-heptenal to produce pentanal; 2-hexenal to produce butanal; ionone to produce 3,3-dimethyl octan-7-onal and acetone; irone to produce 3,3,4-trimethyl octan-7-onal and acetone; 1-(4-methoxyphenyl)-1-penten-3-one to produce paramethoxybenzaldehyde and methyl ethyl ketone; 5-methyl-3-hexen-2-one to produce isobutyraldehyde and acetone; alpha-methyl-iso-ionone to produce citral and methyl ethyl ketone; 5-methyl-2-phenyl-2-hexenal to produce phenylacetaldehyde and 3-methylbutanal; 4-phenyl-3-buten-2-one to produce benzaldehyde and acetone; and ortho-methoxy cinnamaldehyde to produce ortho-methoxy benzaldehyde. Any source of hydrolyzable activated olefin compound may be satisfactorily employed in carrying out the teachings of this invention, ranging from the unprocessed natural or synthetic raw material to a purified extract thereof.

OPERATING EXAMPLES

The following detailed operating examples illustrate the practice of the invention in its most preferred form, thereby enabling a person of ordinary skill in the art to practice the invention. The principles of this invention, its operating parameters and other obvious modifications thereof will be understood in view of the following detailed procedure.

EXAMPLE I

Into a one liter Parr autoclave is placed 80g cassia oil (72% cinnamaldehyde) and 720g H₂O. The autoclave with cassia oil and water is then heated to 250° C. and is held at that temperature for approximately eight hours. The autoclave pressure during the reaction was maintained at 680–700 psi.

At the end of the reaction period, heat and pressure were removed and the autoclave cooled. The organic phase was separated from the water phase by extraction with methylene chloride.

After removal of the majority of the methylene chloride by roto-evaporation, the organic phase was then fractionally distilled. The first fraction to distill was that of benzaldehyde in the amount of 28g. The second fraction recovered was 14g of cinnamaldehyde.

EXAMPLE II

Into a one liter Parr autoclave is placed 80 g cinnamaldehyde and 720 g water. The autoclave containing the starting materials was then heated to 250° C. under 680 psi pressure for approximately eight hours.

After cooling, the organic phase was separated from the water phase by extraction with methylene chloride. After removal of the majority of the methylene chloride by roto-evaporation, the organic phase was then fractionally distilled to provide 23 g benzaldehyde and 23.3 g cinnamaldehyde.

EXAMPLE III

Into a one liter Parr autoclave is placed 80 g cinnamaldehyde and 720 g water. The autoclave was then heated to 250° C. at a pressure of 700 psi for two hours.

After cooling, the organic phase was extracted from the aqueous phase with methylene chloride and fractionally distilled as in Examples I and II. The recovered products were 22 g benzaldehyde and 36.5 g cinnamaldehyde.

EXAMPLE IV

Into a one liter Parr autoclave is placed 720 g water and 80 g terpeneless lemongrass oil containing approximately 95% citral. The autoclave containing the oil and water was then heated to 250° C. at a pressure of 720 psi for two hours.

The contents of the autoclave were then cooled and extracted with methylene chloride. Most of the methylene chloride was removed by roto-evaporation. The separated organic phase was then fractionally distilled, producing 14.16 g 6-methyl-5-hepten2-one, and 9.0 g citral.

EXAMPLE V

Into a 600 ml. Parr autoclave is placed 10 grams 1,2-dibenzoylethylene and 390 grams water. The autoclave was then heated to 275° C. with a resultant pressure of 890 psi for two hours.

After cooling, the organic phase was extracted from the aqueous phase with methylene chloride (100 ml). The solvent was removed in vacuo giving 8.4 grams of oil. Gas chromatographic analysis showed this oil to consist of acetophenone (1.43 g) and 1,2-dibenzoylethylene (1.86 g).

EXAMPLE VI

Into a 600 ml. Parr autoclave is placed 40 grams 4-phenyl-3-buten-2-one and 360 grams water. The autoclave was then heated to 275° C. with a resultant pressure of 920 psi for two hours.

After cooling, the organic phase was extracted from the aqueous phase with methylene chloride (60 ml). The solvent was removed in vacuo yielding 20.7 grams of oil. Gas chromatographic analysis of this oil indicated that it consisted of 9.46 grams benzaldehyde and 10.87 grams 4-phenyl-3-buten-2-one.

EXAMPLE VII

Into a 600 ml. Parr autoclave is placed 10 grams 3-decen-2-one and 390 grams water. The autoclave was then heated to 275° C. with a resultant pressure of 920 psi for two hours.

After cooling, the organic phase was extracted from the aqueous phase with ethyl acetate (60 ml). The solvent was removed in vacuo yielding 4.8 grams of liquid. Gas chromatographic analysis of this oil indicated the oil consisted of 3.01 grams heptanal and 1.49 grams 3-decen-2-one.

EXAMPLE VIII

Into a 600 ml. Parr autoclave is placed 10 grams curcumin [1,7-bis (4-hydroxy-3-methoxyphenyl)1,6-heptadiene-3,5-dione]and water (390 g). The autoclave was then heated to 250° C. with a resultant pressure of 580 psi for two hours.

After cooling, the organic phase was extracted from the aqueous phase with ethyl acetate (60 ml). The solvent was removed in vacuo yielding 7.7 grams of oil. Gas chromatographic analysis of this oil indicated that the oil consisted of 1.07 grams of vanillin [4-hydroxy-3-methoxybenzaldehyde].

EXAMPLE IX

Into a 600 ml. Parr autoclave is placed 330 grams of water. This was then heated to 325° C. and maintained for the time prescribed below. The pressure was regulated so as not to exceed 2000 psi. Once at 325° C. the water was pumped into the autoclave for one minute at a flow rate of 15 ml/minute, the feed line was then switched to cinnamic aldehyde and 40 grams of cinnamic aldehyde containing 0.40 grams (0.45 ml) decahydronaphthalene (internal standard) was pumped into the autoclave followed by 15 ml. of water (total time of addition 5 minutes). The 325° C. temperature was held for 5 minutes at a resultant reactor pressure of 1875 psi. The autoclave was then cooled rapidly (approximately 3 minutes to chill to 200° C.). After cooling to room temperature, the contents were extracted with 400 ml of ethyl acetate. Gas chromatographic analysis of the extract indicated recovery of benzaldehyde (10.40 g) and cinnamic aldehyde (25.20 g)

EXAMPLE X

Into a 600 ml. Parr autoclave is placed 50 mg decane (internal standard), 5.0 grams trans, trans-2,4-decadienal and 395 grams water. The autoclave was then heated to 250° C. with a resultant pressure of 580 psi for two hours.

After cooling, the organic phase was extracted from the aqueous phase with ethyl acetate (400 ml). Gas chromatographic analysis of this oil indicated the organic phase consisted of 0.62 grams hexanal and 0.49 grams decadienal plus several decadienal rearranged products.

It is also possible to conduct the hydrolysis reaction on a continuous basis. The activated olefin and water can be pumped through a heated stainless steel tube having a back-pressure regulator which can maintain a pressure in the tube slightly greater than that of steam. Parameters which would affect the conversion rate of the activated olefin are the concentration of the olefin in water, the temperature of the tube, and the residence time of the olefin-water mixture in the tube.

Thus, it can be seen that by following the teachings of this invention, one can hydrolyze acyclic unsaturated conjugated ketones and aldehydes by either batch or continuous processes to produce desirable cleavage products in good yield. The amount of yield obtained is surprising in that heretofore the hydrolysis of such acyclic ketones and aldehydes was not known to proceed at all without the presence of an alkaline catalyst. It is now possible to hydrolyze olefinic compounds activated by the carbonyl group of a ketone or aldehyde substituent using only water, heat, and pressure.

Having described this invention, and its operating parameters, variations may be achieved without departing from the spirit and scope hereof.

What is claimed is:

1. A method of hydrolyzing an activated olefin to produce a carbonyl-containing compound comprising:
    reacting an acyclic olefin selected from the group consisting of 1,2-dibenzoylethylene, 4-phenyl-3-buten-2-one and 3-decen-2-one at substantially neutral pH in the presence of water, and
    heating at a pressure of about 225 to about 2000 psi sufficient to effect said hydrolysis reaction.

2. The method of claim 1 wherein the temperature is at least about 200° C. and the pressure is at least about 225 psi.

3. The method of claim 1 wherein the temperature is o the order of about 200° C. to about 325° C. and a pressure on the order of about 225 to about 2000 psi.

4. The method of claim 1 wherein the reaction is conducted in an autoclave or other pressure reactor.

5. The method of claim 1 wherein the hydrolysis reaction is effected continuously in a tube reactor.

6. The method of claim 1 wherein the volume of water exceeds the volume of activated olefin.

* * * * *

UNITED STATES PATENT AND TRADEMARK OFFICE
CERTIFICATE OF CORRECTION

PATENT NO. : 4,871,881
DATED      : October 3, 1989
INVENTOR(S) : Joseph E. Dolfini et al It is certified that error appears in the above-identified patent and that said Letters Patent is hereby corrected as shown below:

Column 2, line 6, "eta" should be --beta--.

Column 2, line 47, "t" should be --to--.

Column 4, line 2, "28g" should be --18g--.

Column 4, lines 14, & 15, "23.3g" should be --13.3g--.

Column 4, line 38, "6-methyl-5-hepten2-one" should be
    --6-methyl-5-hepten-2-one--.

Signed and Sealed this

Twenty-eighth Day of August, 1990

Attest:

HARRY F. MANBECK, JR.

*Attesting Officer*         *Commissioner of Patents and Trademarks*